(12) United States Patent
Bruzadin et al.

(10) Patent No.: US 8,034,991 B2
(45) Date of Patent: Oct. 11, 2011

(54) ABSORBENT ARTICLE INCLUDING A PLURALITY OF LONGITUDINALLY EXTENDING CHANNELS

(75) Inventors: Fernanda Bruzadin, São José dos Campos (BR); Francisco J. V. Hernandez, São Jose dos Campos (BR); Fernanda Wiermann Paques, São Jose dos Campos (BR)

(73) Assignee: Johnson & Johnson Ind. E Com. Ltda (BR)

( * ) Notice: Subject to any disclaimer, the term of this patent is extended or adjusted under 35 U.S.C. 154(b) by 230 days.

(21) Appl. No.: 12/431,793

(22) Filed: Apr. 29, 2009

(65) Prior Publication Data

US 2010/0280474 A1    Nov. 4, 2010

(51) Int. Cl.
*A61F 13/15* (2006.01)

(52) U.S. Cl. .. 604/378; 604/380; 604/381; 604/385.101
(58) Field of Classification Search ................... 604/378, 604/380, 381, 385.101
See application file for complete search history.

(56) References Cited

U.S. PATENT DOCUMENTS 4,623,340 A * 11/1986 Luceri ...................... 604/385.05
7,223,900 B1 * 5/2007 Lariviere et al. .............. 604/380

* cited by examiner

*Primary Examiner* — Jacqueline F. Stephens (57) ABSTRACT

An absorbent article including a first end region, a second end region and a central region, a plurality of channels arranged in each of the first and second end regions, at least one channel arranged in the central region and extending in a longitudinal direction of the article, the at least one channel being connected at each end thereof to the plurality of channels in the first end region and the plurality of channels in the second end region.

19 Claims, 6 Drawing Sheets

ABSORBENT ARTICLE INCLUDING A PLURALITY OF LONGITUDINALLY EXTENDING CHANNELS

FIELD OF INVENTION

The present invention generally relates to absorbent sanitary napkins and in particular to a sanitary napkin including a plurality of longitudinally extending channels for promoting enhanced fluid wicking in the longitudinal direction of the napkin.

BACKGROUND OF THE INVENTION

In order for a sanitary napkin to efficiently absorb a large amount of fluid during use it must effectively wick fluid throughout the absorbent structure of the napkin. Absent effective wicking properties menstrual fluid tends to pool in certain regions of the napkin as a result of which the full absorbent capacity of the napkin is not effectively utilized. In addition to having superior wicking capabilities, sanitary napkins must also be able to quickly absorb fluid. That is, sanitary napkins must also have superior fluid penetration characteristics. Accordingly, the inventors of the present invention have recognized a need to provide a sanitary napkin that efficiently wicks fluid in the longitudinal direction of the napkin while at the same time providing superior fluid penetration characteristics. By providing a napkin that efficiently wicks fluid in the longitudinal direction, while at the same time quickly absorbs fluid, the inventors have provided a sanitary napkin that exhibits superior fluid handling characteristics and effectively utilizes the full absorbent capacity of the napkin.

SUMMARY OF THE INVENTION

In view of the foregoing, the present invention provides, according to a first aspect of the invention, an absorbent article including a longitudinally extending centerline, a transversely extending centerline, a first end region and a second end region, a central region arranged between the first and second end regions, a first longitudinal edge, a second longitudinal edge, a first transverse edge, a second transverse edge, a plurality of interconnected channels arranged in each of the first and second end regions, at least one channel arranged in the central region and extending in a longitudinal direction of the article, the at least one channel intersecting at each end at least one of the plurality of interconnected channels in the first end region and at least one of the plurality of interconnected channels in the second end region.

BRIEF DESCRIPTION OF THE DRAWINGS

Examples of embodiments of the present invention will now be described with reference to the drawings, in which.

DETAILED DESCRIPTION OF THE INVENTION

The present invention generally relates to disposable absorbent articles such as sanitary napkins, pantiliners, absorbent products for incontinence, and other disposable absorbent articles worn close to a wearer's body. Although the invention will be described herein with reference to a sanitary napkin 10, the invention may be utilized with other disposable sanitary absorbent articles such as absorbent products for incontinence, diapers, pantiliners and the like.

Absorbent articles according to the present invention provide superior fluid handling characteristics, and more specifically provide superior longitudinal wicking characteristics. In addition, absorbent articles according to the present invention provide superior fluid penetration characteristics.

Figure 1:
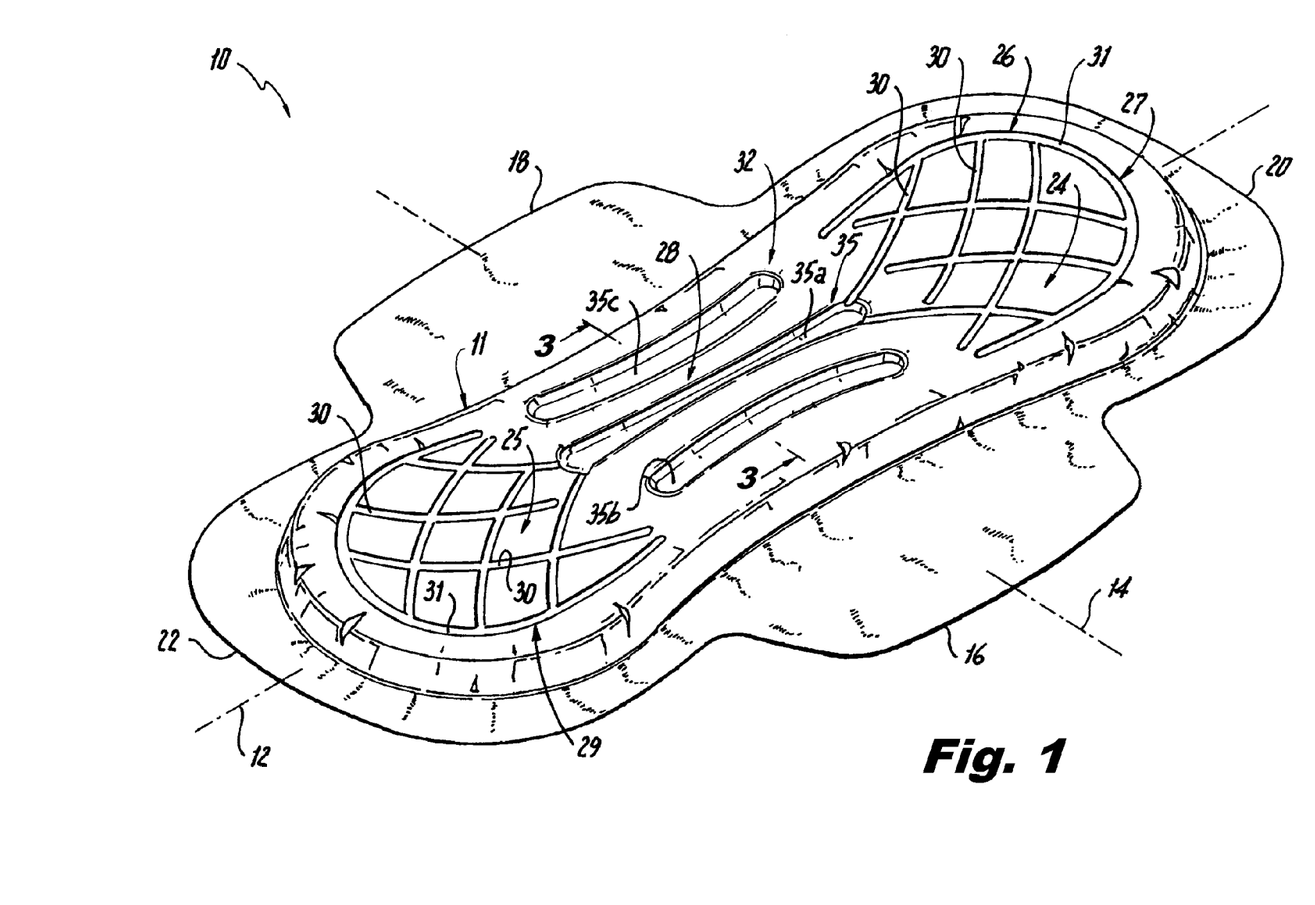
FIG. 1 is a perspective view of an absorbent article according to a first embodiment of the present invention.

A specific embodiment of a sanitary napkin 10 according to the present invention is illustrated in FIG. 1. The sanitary napkin 10 includes a longitudinally extending centerline 12, a transversely extending centerline 14, a first longitudinal edge 16, a second longitudinal edge 18, a first transverse edge 20, a second transverse edge 22, a first end region 24, a second end region 25, and a central region 28 located between the first end second end regions, 24 and 25.

The napkin 10 further includes a first embossing pattern 26. The first embossing pattern 26 has a first portion 27 arranged in the first end region 24 and a second portion 29 located in the second end region 25, thus the first and second portions 27 and 29 are spaced from one another in the longitudinal direction of the napkin 10. Each of the first portion 27 and second portion 29 comprise a plurality of interconnected arcuate channels 30, each one of the channels 30 extending from one side of the napkin, across the longitudinally extending centerline 12, to the other side of the napkin. Each one of the channels 30 intersects at least one other channel 30 at an oblique angle relative thereto and each one of the channels 30 extends across the longitudinally extending centerline 12 at an oblique angle relative thereto. Each of the first and second portions 27 and 29 further include a substantially U-shaped end channel 31. Each of the channels 30, at a distal portion thereof (i.e. that portion of the channel 30 located furthest from the intersection of the longitudinally extending centerline 12 and transversely extending centerline 14), intersect with, and terminate at, the end channel 31.

Each of the channels 30 is substantially arcuate in shape and has a length in the range of about 2 cm to about 10 cm, more preferably from about 5.0 cm to about 8.0 cm, when measured along the path of the channel 30. Each of the channels 30 has a width in the range of from about 1 mm to about 10 mm, more preferably from about 2 mm to about 4.0 mm. Each of the channels 30 has a depth of about 0.5 mm to about 5 mm, more preferably about 1 mm to about 3 mm, when measured from a top surface of the napkin 10. Each end channel 31 has a length in the range of about 5 cm to about 25 cm, more preferably from about 10 cm to about 15 cm. Each end channel 31 has a depth of about 0.5 mm to about 5 mm, more preferably about 1 mm to about 3 mm, when measured from a top surface of the napkin 10.

The channels 30 function to transport fluid towards the ends regions 24, 25 of the napkin 10 to thereby utilize the full absorbent capacity of the article along its length. The end channels 31 function to prevent fluid from being transported to the very end the napkin and in this manner serve to prevent end leakage, that is the leakage of fluid beyond the transverse edges 20 and 22 of the napkin. In this regard, each of the channels 31 are preferably spaced from a respective transverse edge, 20 and 22 respectively, of the napkin by a distance of from about 5 mm to about 30 mm, more preferably from about 10 mm to about 20 mm.

The napkin 10 further includes a second embossing pattern 32. The second embossing pattern 32 is generally located in the central region 28 of the napkin 10. The second embossing pattern 32 includes at least one longitudinally extending channel 35. Absorbent articles according to the present invention preferably have between about 1 and about 5 channels 35. In the specific embodiment shown in FIG. 1, the second embossing pattern 32 includes three generally longitudinally extending channels 35a, 35b and 35c. The longitudinally extending channel 35a is coextensive with the longitudinally extending centerline 12 and arranged symmetrically with respect thereto. Each of the channels 35b and 35c are arranged in spaced relationship to channel 35a and generally have an arcuate shape. In addition, channels 35b and 35c are symmetrically arranged relative to the longitudinally extending centerline 12 and are shaped such that they are concave relative to the longitudinally extending centerline 12. Each one of the channels, 35a, 35b, and 35c preferably has a length in the range of about 3 cm to about 15 cm, more preferably from about 4.5 cm to about 10 cm, when measured along a path of the channel. Each of the channels, 35a, 35b and 35c preferably has a width in the range of from about 1 mm to about 20 mm, more preferably from about 2 mm to about 10 mm. Each of the channels 35a, 35b and 35c preferably has a depth in the range of from about 1 mm to about 10 mm, more preferably between about 2 mm and about 5 mm.

Preferably, at least one of the channels 35a, 35b, and 35c intersects at least one of the channels 30 in the first end region 24 and at least one of the channels 30 in the second end region 25. In the specific embodiment of the invention shown in FIG. 1, channel 35a intersects, at respective ends thereof, a channel 30 in the first end region 24 and another channel 30 located in the second end region 25. The interconnection of channel 35a with the first 27 and second 29 portions of the first embossing pattern 26 enable the sanitary napkin 10 to effectively wick fluid from the central region 28 of the napkin 10 to the end regions 24 and 25 of the napkin. In this manner, the full absorbent capacity of the napkin 10 is utilized.

Figures 2, 3:
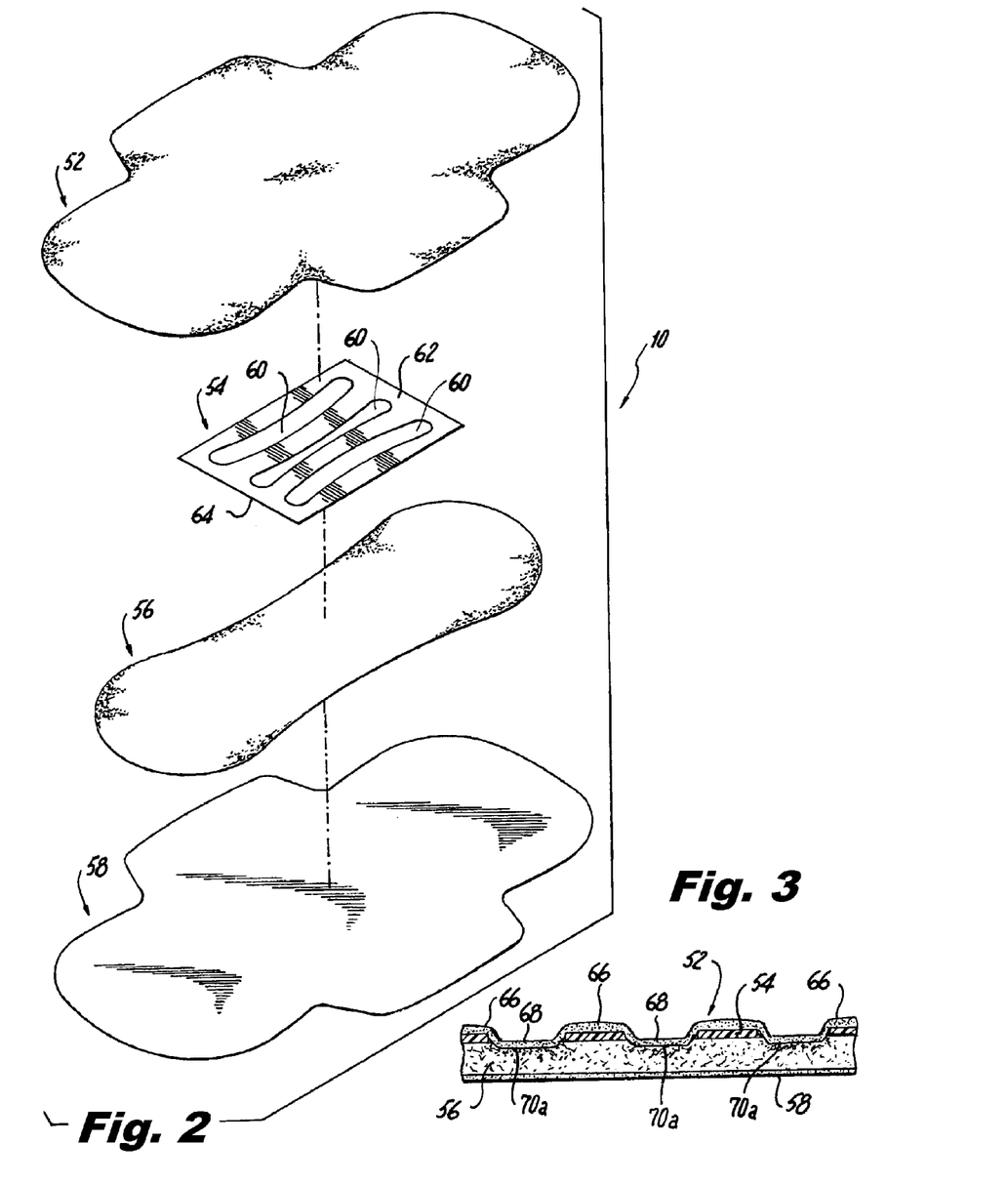
FIG. 2 is an exploded view of the absorbent article shown in FIG. 1 depicting the constituent material layers thereof prior to embossing.
FIG. 3 is a sectional view taken along line 3-3 in FIG. 1.

In one embodiment of the invention, as best seen in the exploded view shown in FIG. 2, the sanitary napkin 10 includes a fluid permeable cover layer 52, a first absorbent layer 54, a second absorbent layer 56, and a fluid impermeable barrier layer 58. The first absorbent layer 54 includes a plurality of longitudinally extending material-free zones 60 that extend from an upper surface 62 of the first absorbent layer 54 to a lower surface 64 of the first absorbent layer 54. Each of the material-free zones 60 preferably has a length of from about 3 cm to about 15 cm, more preferably from about 4.5 cm to about 10 cm, when measured along a path of the material-free zone 60. Each of the material-free zones 60 preferably has a width in the range of from about 1 mm to about 20 mm, more preferably from about 2 mm to about 10 mm. It is noted that each of the material-free zones corresponds in size, shape and location to channels 35a, 35b, and 35c.

Absorbent articles according to the present invention preferably have between about 1 and about 5 longitudinally extending the material-free zones 60. Each of the material-free zones 60 is spaced from an adjacent material-free zone 60 in the transverse direction by a distance from about 0.5 cm to about 3 cm. The material-free zones 60 preferably extend over a surface area in the range of between 50 mm$^2$ and about 4000 mm$^2$.

As best seen in FIG. 3, the cover layer 52 includes a plurality of first regions 66 that are arranged in spaced relationship to the second absorbent layer 56 and a plurality of second regions 68 that are arranged in surface to surface contact with the second absorbent layer 56. This structure is formed during manufacture of the sanitary napkin 10 by utilizing an embossing roll having a surface pattern corresponding in size and shape to channels 35a, 35b, and 35c. Specifically, the cover 52 is embossed such that the regions 68 of the cover 52 are arranged in surface to surface contact with the second absorbent layer 56. Further, also during the embossing process, the second absorbent layer 56 is embossed to form channels 70a, 70b and 70c in the second absorbent layer 56 that correspond in shape and location to the channels 35a, 35b, and 35c. Of course, the embossing roll used during manufacture should also have surface features used to form the first embossing pattern 26.

The arrangement of the regions 68 in surface to surface contact with the second absorbent layer 56 permits the sanitary napkin 10 according to the present invention to quickly absorb fluid in the center of the napkin where such "gush management" is required. Also, the regions 66 of the cover, in cooperation with the channels 32, permit the effective wicking of fluid to the end regions 24 and 25 of the napkin. In this manner, the sanitary napkin 10 according to the present invention can provide effective "gush management" while at the same time effectively utilizing the full absorbent capacity of the napkin 10 along its length.

Figures 4, 5, 6:
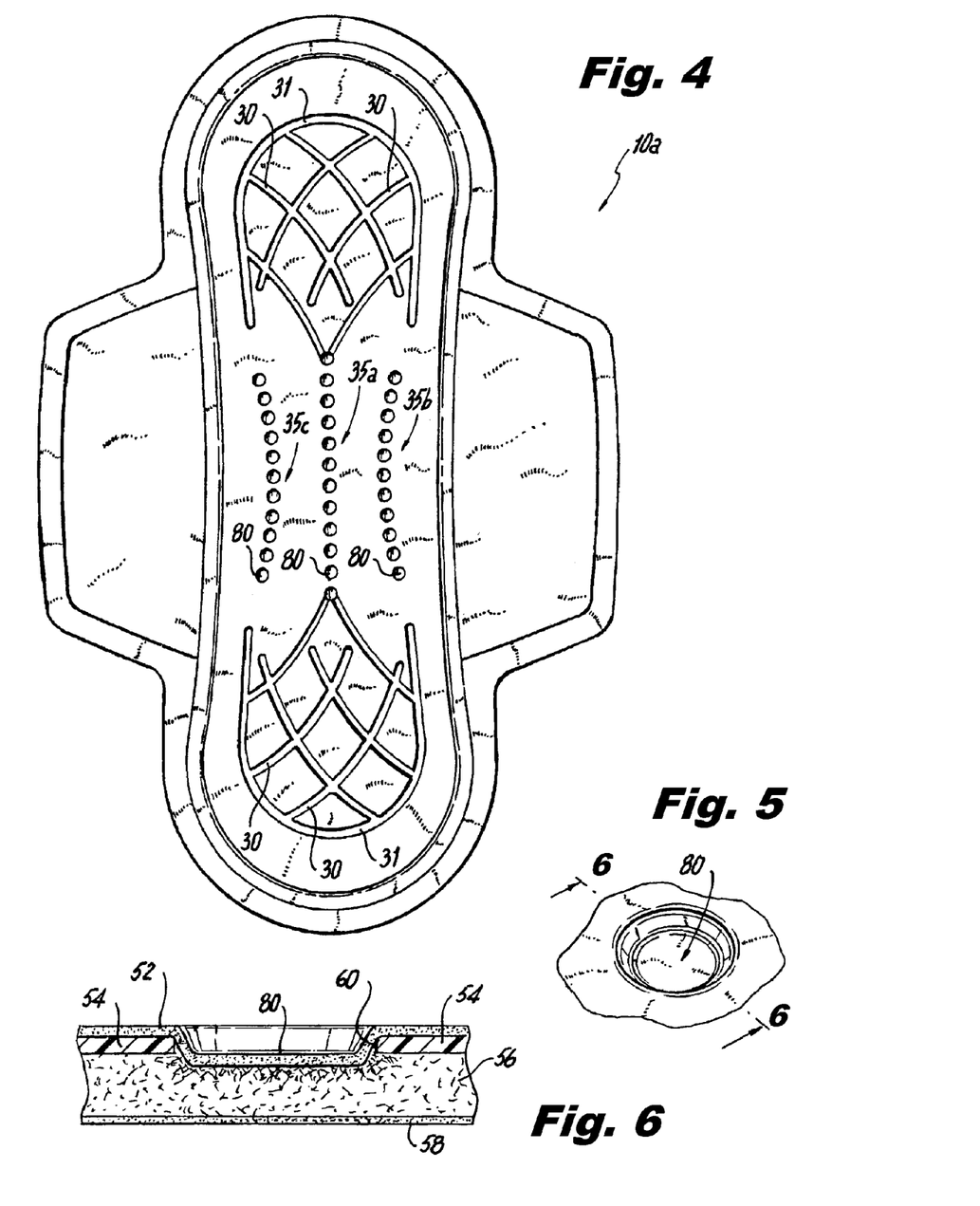
FIG. 4 is a top plan view of an absorbent article according to a second embodiment of the present invention.
FIG. 5 is a detailed perspective view of a portion of the absorbent article shown in FIG. 4.
FIG. 6 is a sectional view taken along line 6-6 in FIG. 5.

A sanitary napkin 10a, according to second embodiment of the present invention, is depicted in FIGS. 4-6. The sanitary napkin 10b has substantially the same structure, as sanitary napkin 10 described above. However, in the embodiment of the invention shown in FIGS. 4-6 the "channels" 35a, 35b and 35c are not continuous, as in napkin 10 described above, but rather are formed from a plurality of discretely arranged depressed regions 80. As shown in FIG. 4, each depressed region 80 is arranged in spaced relationship to an adjacent depressed region 80. The depressed regions 80 collectively cooperate to define "interrupted" channels 35a, 35b and 35c. In the particular embodiment of the invention shown in FIGS. 4-6 each depressed region 80 is circular in shape, as shown in detail in FIG. 5. In the embodiment shown in FIGS. 4-6, the first absorbent layer 54 includes a plurality of material-free zones 60 that each correspond in shape, size and location to a corresponding depressed region 80, one of such material-free zones 60 and corresponding depressed regions 80 being depicted in detail in FIG. 6.

Figures 7, 8, 9:
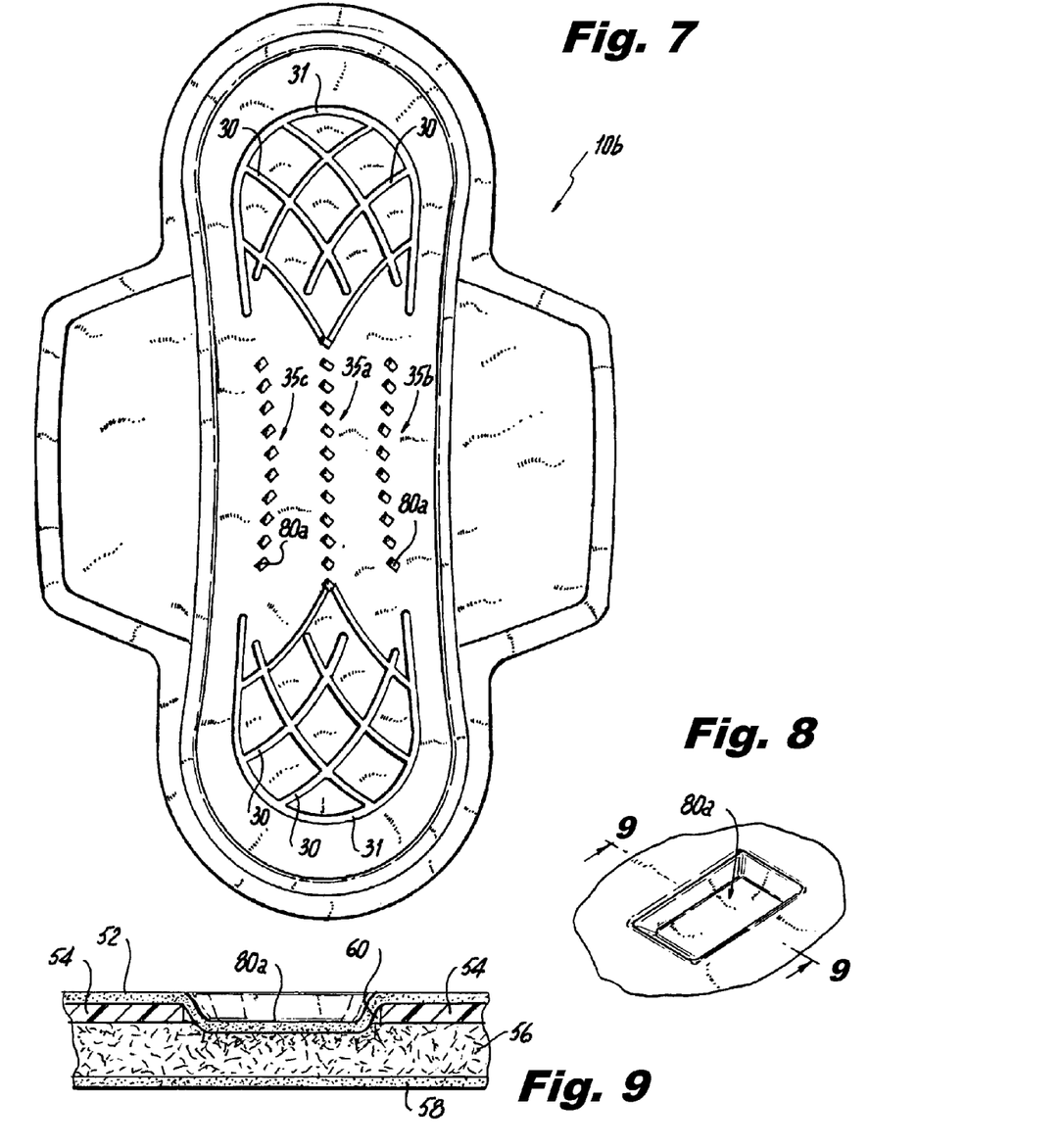
FIG. 7 is a top plan view of an absorbent article according to a third embodiment of the present invention.
FIG. 8 is a detailed perspective view of a portion of the absorbent article shown in FIG. 7.
FIG. 9 is a sectional view taken along line 9-9 in FIG. 8.

A sanitary napkin 10b, according to third embodiment of the present invention, is depicted in FIGS. 7-9. The sanitary napkin 10c has substantially the same structure, as sanitary napkin 10b described above with reference to FIGS. 4-6. However, in the embodiment of the invention depicted in FIGS. 7-9 each depressed region 80a is rectangular or diamond in shape, as shown in detail in FIG. 8.

Figure 10:
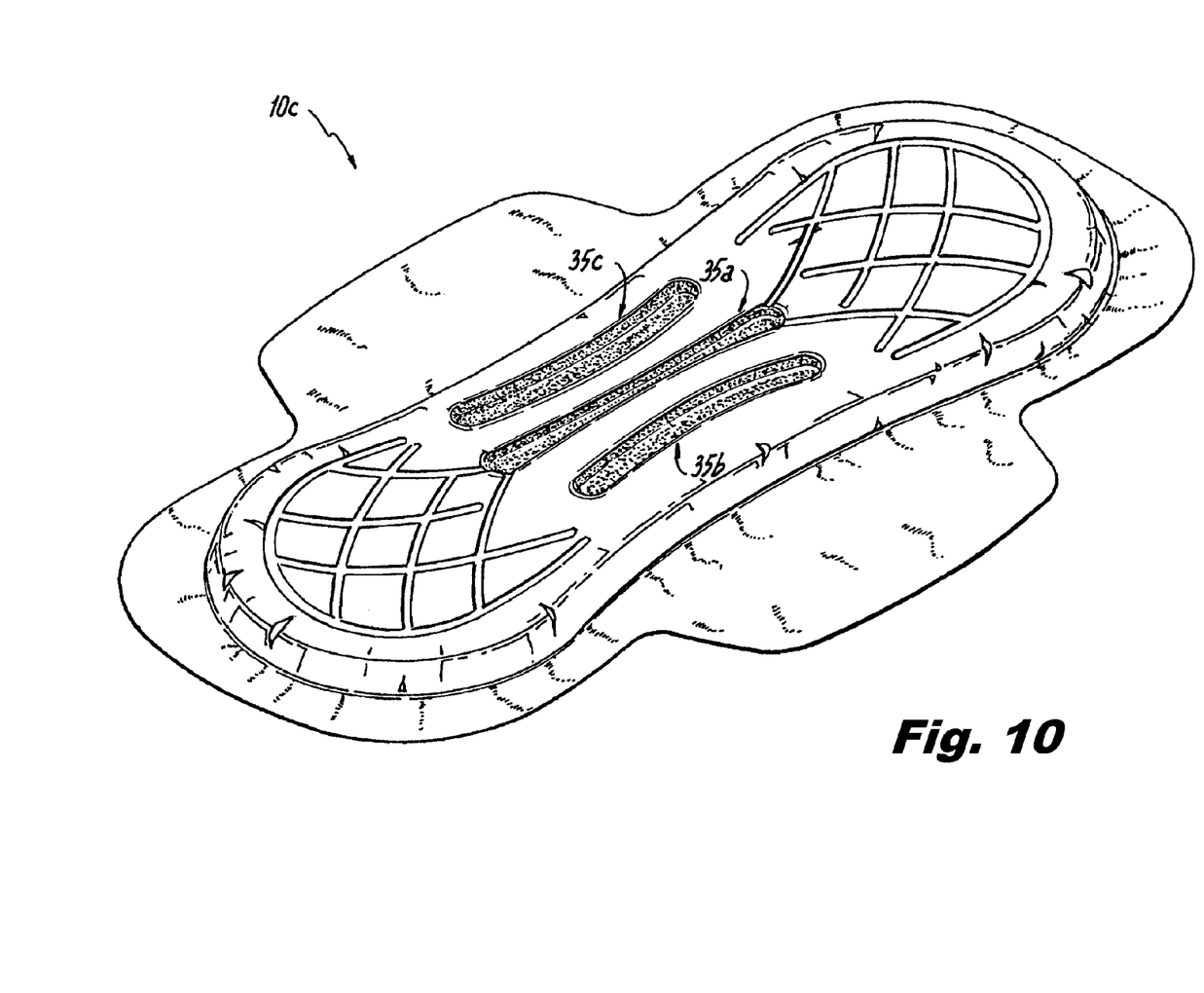
FIG. 10 is a perspective view of an absorbent article according to a fourth embodiment of the present invention.
Figure 11:
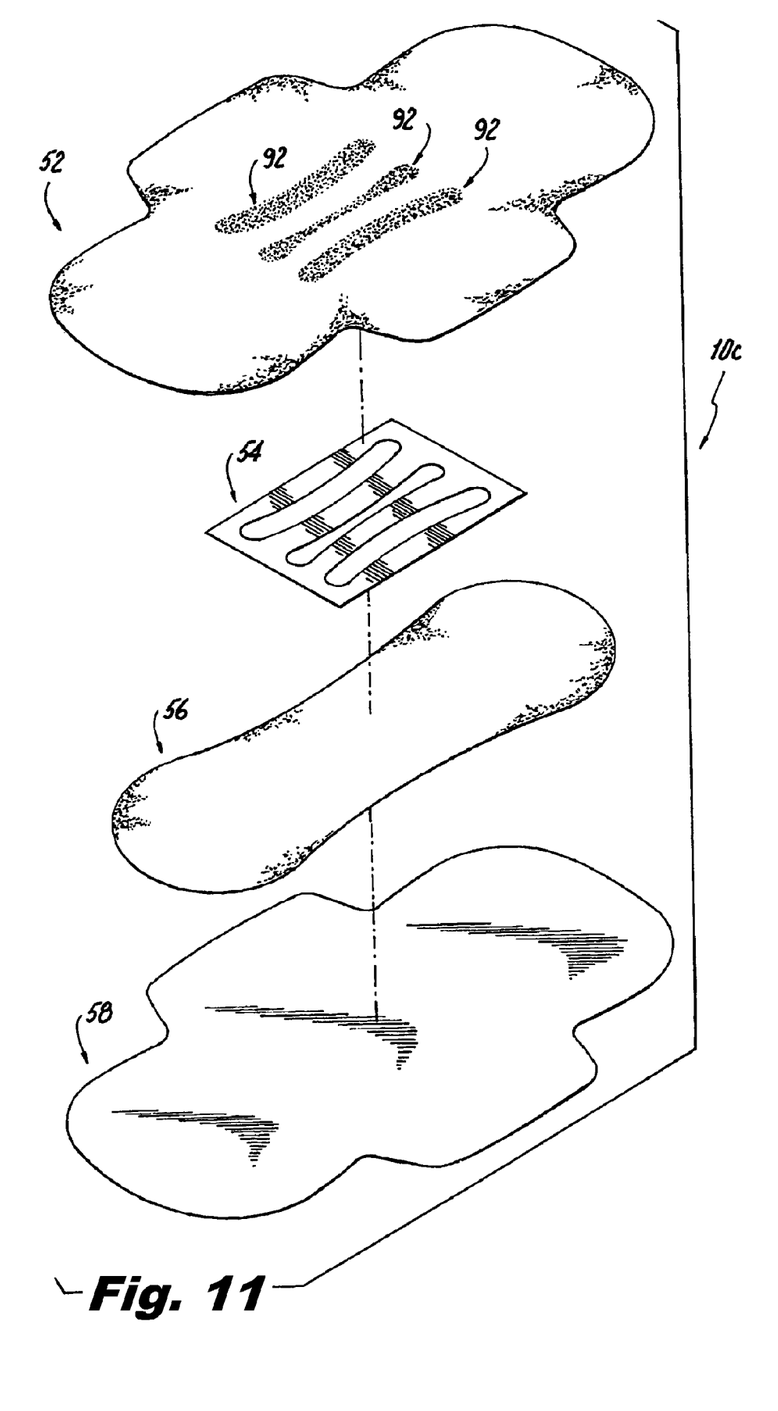
FIG. 11 is an exploded view of the absorbent article shown in FIG. 11, depicting the constituent material layers thereof prior to embossing.

A sanitary napkin 10c, according to a fourth embodiment of the present invention, is depicted in FIGS. 10-11. The sanitary napkin 10c has substantially an identical structure to sanitary napkin 10 described above. However, as shown in FIG. 10, the channels 35a, 35b and 35c are provided with color, to thereby provide a color cue that is visible to a user from a top surface of the napkin 10c. As shown in FIG. 11, the color cue may be provided by printing colored regions 92 to the cover layer 52. The colored regions 92 preferably correspond in size, shape and location to the channels 35a, 35b, and 35c. The colored regions 92 function provide the user with a color cue to the presence and function of the channels 35a, 35b and 35c. The colored regions 92 could alternatively be printed on the second absorbent layer 56 provided that such colored regions 92 can be viewed through the cover 52. Any means known to those of skill in the art may be utilized to provide the colored regions 92 such as printing, utilizing colored fibers, or any other suitable means.

Cover Layer

The cover layer 52 may be a relatively low density, bulky, high-loft non-woven web material. The cover layer 52 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 52 has a basis weight in the range of about 10 gsm to about 75 gsm.

Bi-component fibers may be made up of a polyester layer and a polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the absorbent layer and/or to the barrier layer.

The cover layer 52 preferably has a relatively high degree of wettability, although the individual fibers comprising the cover may not be particularly hydrophilic. The cover material should also contain a great number of relatively large pores. This is because the cover layer 52 is intended to take-up body fluid rapidly and transport it away from the body and the point of deposition. Therefore, the cover layer contributes little to the time taken for the napkin to absorb a given quantity of liquid (penetration time).

Advantageously, the fibers which make up the cover layer 52 should not lose their physical properties when they are wetted, in other words they should not collapse or lose their resiliency when subjected to water or body fluid. The cover layer 52 may be treated to allow fluid to pass through it readily. The cover layer 52 also functions to transfer the fluid quickly to the underlying layers of the napkin. Thus, the cover layer 52 is advantageously wettable, hydrophilic and porous. When composed of synthetic hydrophobic fibers such as polyester or bi-component fibers, the cover layer 52 may be treated with a surfactant to impart the desired degree of wettability.

Alternatively, the cover layer 52 can also be made of polymer film having large pores. Because of such high porosity, the film accomplishes the function of quickly transferring body fluid to the inner layers of the underlying absorbent layers. A suitable cover material of this type is commercially found on the STAYFREE Dry Max Ultrathin product distributed by McNeil-PPC, Inc.

The cover layer 52 may be attached to the underlying absorbent layers 54 and 56, and/or the barrier layer 58, by adhesion and/or other suitable means know to those of skill in the art.

First Absorbent Layer

The first absorbent layer 54 may be composed of fibrous materials, such as wood pulp, polyester, rayon, flexible foam, or the like, or combinations thereof. The first absorbent layer 54 may also optionally include a superabsorbent polymer (SAP) material. The first absorbent layer 54 may also comprise thermoplastic fibers for the purpose of stabilizing the layer and maintaining its structural integrity. The first absorbent layer 54 may be treated with surfactant on one or both sides in order to increase its wettability, although generally the first absorbent layer 54 is relatively hydrophilic and may not require treatment. The first absorbent layer 54 is preferably bonded on both sides to the adjacent layers, i.e. the cover layer 52 and the underlying second absorbent layer 56.

In specific embodiments of the present invention the first absorbent layer 54 may be a "transfer" layer. The transfer layer provides means for receiving body fluid from the fluid-pervious cover layer 52 and holding it until the second absorbent layer 54 has an opportunity to absorb it. The transfer layer is, preferably, more dense than the fluid-pervious cover layer 52 and has a larger proportion of smaller pores than does the latter. These attributes allow the transfer layer to contain body fluid and hold it away from the outer side of the fluid-pervious cover layer 52, thereby preventing the fluid from re-wetting the fluid-pervious cover layer 54 and its surface. However, the transfer layer is preferably not so dense as to prevent the passage of the fluid through the transfer layer and into the underlying second absorbent layer 54.

When constructed as a transfer layer, the first absorbent layer 52 may comprise various materials, including, for example, cellulose fibers such as from wood pulp, single component or bicomponent fibers that include thermoplastic materials (such as polyester, polypropylene, polyethylene, among others) in fiber or other forms, rayon, organic binders (such as copolymers of vinyl, acrylic and/or other monomers that may be coated onto thermoplastic fibers or otherwise incorporated into the transfer layer) among other materials known to the art.

Second Absorbent Layer

The second absorbent layer 56 may comprise a single layer of material or may comprise multiple layers. In preferred embodiments of the present invention the second absorbent layer 56 functions as the absorbent core of the sanitary napkin 10. In preferred embodiments of the present invention the second absorbent layer 56 functions as an absorbent core. Preferably, such absorbent core has a high total absorbent capacity and function to hold fluid upon receiving such fluid from the transfer layer. In addition, the absorbent core preferably has a greater density than that of the transfer layer.

In one embodiment, the second absorbent layer 56 is a blend or mixture of cellulosic fibers and superabsorbent disposed therein. Cellulosic fibers that can be used in the second absorbent layer 56 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material. Some portion of the pulp may be chemically treated as discussed in U.S. Pat. No. 5,916,670 to improved flexibility of the product. Flexibility of the material may also be improved by mechanically working the material or tenderizing the material.

The second absorbent layer 56 can contain any superabsorbent polymer (SAP) which are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA70N and products offered by Stockhausen Inc. In a specific example, the second absorbent layer 56 is a material containing from 90% to about 40% percent cellulosic fiber, about 10% to about 60% SAP. The second absorbent layer 56 may comprise a material manufactured by using air-laying means well known in the art.

Barrier Layer

Underlying the second absorbent layer 56 is a barrier layer 58 comprising liquid-impervious film material so as to prevent liquid that is entrapped in the absorbent layer 56 from egressing the sanitary napkin and staining the wearer's undergarment. The barrier layer 58 is preferably made of polymeric film, although it may be made of liquid impervious, air-permeable material such as repellent-treated non-woven or micropore films or foams.

The barrier layer 58 may be breathable, i.e., permits vapor to transpire. Known materials for this purpose include non-woven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 52 and the barrier layer 58 are preferably joined along their marginal portions so as to form an enclosure or flange seal that maintains the absorbent layers 54 and 56 captive. The joint may be made by means of adhesives, heat-bonding, ultrasonic bonding, radio frequency sealing, mechanical crimping, and the like and combinations thereof.

Positioning adhesive may be applied to a garment facing surface of the barrier layer 58 for securing the napkin 10 to a garment during use. The positioning adhesive may be covered with removable release paper so that the positioning adhesive is covered by the removable release paper prior to use.

Absorbent articles of this invention may or may not include wings, flaps or tabs for securing the absorbent article to an undergarment. Wings, also called, among other things, flaps or tabs, and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear.

As illustrated by the above description and the accompanying drawings absorbent articles according to the present invention provide a structure that enables such article to provide superior wicking characteristics while at the same time providing superior fluid penetration characteristics.

We claim:

1. An absorbent article comprising:
   a longitudinally extending centerline;
   a transversely extending centerline;
   a first end region and a second end region;
   a central region arranged between the first and second end regions;
   a first longitudinal edge;
   a second longitudinal edge;
   a first transverse edge;
   a second transverse edge;
   a first embossing pattern having a first portion located in the first end region and a section portion located in the second end region, each of the first portion and second portion including a plurality of interconnected channels arranged in each of the first and second end regions;
   a second embossing pattern including at least one channel arranged in the central region and extending in a longitudinal direction of the article, the at least one channel intersecting at least one of the plurality of interconnected channels in the first end region and at least one of the plurality of interconnected channels in the second end region; and
   wherein the plurality of channels in the first end region are arranged in spaced relationship to the plurality of channels in the second end region.

2. The absorbent article according to claim 1, wherein the plurality channels in the first and second end regions comprise a plurality of arcuate channels, each one of the arcuate channels extending across the absorbent article from one side of the longitudinally extending centerline to the other side of the longitudinally extending centerline.

3. The absorbent article according to claim 2, wherein each of the arcuate channels intersects at least one other arcuate channel at an oblique angle relative thereto and each of the arcuate channels extends across the longitudinally extending centerline at an oblique angle relative thereto.

4. The absorbent article according to claim 1, further comprising a first end channel located in the first end region and a second end channel located in the second end region, each one of the plurality of channels in the first end region intersecting with and terminating at the first end channel, each one of the plurality of channels in the second end region intersecting with and terminating at the second end channel.

5. The absorbent article according to claim 1, wherein the first end channel and the second end channel are substantially U-shaped, the first end channel being spaced inwardly relative to a first transverse edge of the article and the second end channel being spaced inwardly relative to a second transverse edge of the article.

6. The absorbent article according to claim 1, wherein the at least one longitudinally extending channel comprises a plurality of longitudinally extending channels, one of the longitudinally extending channels being substantially coextensive with the longitudinally extending centerline of the article, and the other longitudinally extending channels being arranged in spaced relationship to the channel that is substantially coextensive with the longitudinally extending centerline.

7. The absorbent article according to claim 6, wherein the longitudinally extending channel that is substantially coextensive with the longitudinally extending centerline intersects at least one of the plurality of channels in the first end region and at least one of the plurality of channels in the second end region.

8. The absorbent article according to claim 7, wherein the absorbent article comprises:
- a cover layer;
- a barrier layer;
- a first absorbent layer and a second absorbent layer arranged between the cover layer and the barrier layer, the first absorbent layer being arranged adjacent the cover layer and the second absorbent layer being arranged adjacent to the first absorbent layer;
- wherein the first absorbent layer including a plurality of longitudinally extending material-free zones, each one of the material-free zones corresponding in size, shape and location to a corresponding one of the longitudinally extending channels.

9. The absorbent article according to claim 8, wherein the cover layer includes a plurality of first regions arranged in spaced relationship to the second absorbent layer and a plurality of second regions arranged in surface to surface contact with the second absorbent layer.

10. The absorbent article according to claim 9, wherein each one of the plurality of second regions is located within one of the material-free zones of the first absorbent layer.

11. The absorbent article according to claim 10, wherein the second absorbent layer is provided with a plurality of channels each one of the plurality of channels corresponding in shape and location to a corresponding one of the plurality of longitudinally extending channels.

12. The absorbent article according to claim 11, wherein each one of the plurality of channels in the second absorbent layer corresponds in shape and location to a corresponding one of the material-free zones.

13. The absorbent article according to claim 12, wherein each one of the plurality of longitudinally extending channels is a continuous channel.

14. The absorbent article according to claim 12, wherein each one of the plurality of longitudinally extending channels comprises a plurality of discretely arranged depressed regions.

15. The absorbent article according to claim 14, wherein each one of the plurality of discretely arranged depressed regions is arranged in spaced relationship to an adjacent one of the plurality of discretely arranged depressed regions.

16. The absorbent article according to claim 15, wherein each one of the depressed regions is circular in shape.

17. The absorbent article according to claim 15, wherein each one of the depressed regions is rectangular in shape.

18. The absorbent article according to claim 15, wherein each one of the depressed regions is diamond in shape.

19. The absorbent article according to claim 12, wherein each of the plurality of longitudinally extending channels is provided with a color cue visible from a top surface of the article.

* * * * *